United States Patent
Pavani

(10) Patent No.: US 9,395,309 B2
(45) Date of Patent: Jul. 19, 2016

(54) MULTIPLE ANGLE COMPUTATIONAL WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Palo Alto, CA (US)

( * ) Notice: Subject to any disclaimer, the term of this patent is extended or adjusted under 35 U.S.C. 154(b) by 0 days.

(21) Appl. No.: 14/514,406

(22) Filed: Oct. 15, 2014

(65) Prior Publication Data

US 2016/0109381 A1     Apr. 21, 2016

(51) Int. Cl.
*G01N 21/95* (2006.01)
*G01N 21/88* (2006.01)

(52) U.S. Cl.
CPC ........ *G01N 21/9501* (2013.01); *G01N 21/8851* (2013.01); *G01N 2201/06113* (2013.01); *G01N 2201/12* (2013.01)

(58) Field of Classification Search
CPC .................. G01N 21/95; G01N 21/47; G01N 2021/4711; G01N 2021/8822; G01N 2021/4186; G01N 2021/8928; G06T 7/0004; G01B 11/24

USPC ............ 356/600–623, 237.1–237.5, 445–448
See application file for complete search history.

(56) References Cited

U.S. PATENT DOCUMENTS

| | | | |
|---|---|---|---|
| 4,532,723 A * | 8/1985 | Kellie | G01B 11/00 209/579 |
| 5,087,822 A * | 2/1992 | Fairlie | G01N 21/8903 250/559.16 |
| 6,587,193 B1 | 7/2003 | Reinhron et al. | |
| 7,525,649 B1 | 4/2009 | Leong et al. | |
| 7,724,362 B1 | 5/2010 | Rosengaus | |
| 2009/0161095 A1* | 6/2009 | Taniguchi | G01N 21/9501 356/237.2 |
| 2011/0141463 A1* | 6/2011 | Chikamatsu | G01N 21/956 356/237.5 |
| 2011/0169944 A1 | 7/2011 | Zhao et al. | |
| 2011/0176146 A1* | 7/2011 | Alvarez Diez | G01B 11/002 356/601 |

* cited by examiner

*Primary Examiner* — Hoa Pham

(57) ABSTRACT

A system and method for inspecting a surface, comprising: illuminating a region of said surface, with said region having an aspect ratio larger than unity; capturing an image of scattered radiation originating from said region; and computing electromagnetic field of said scattered radiation from said image of scattered radiation and generating an image of region by computational propagation of said electromagnetic field through a predetermined distance, whereby features of said region are captured in said image of region.

20 Claims, 7 Drawing Sheets

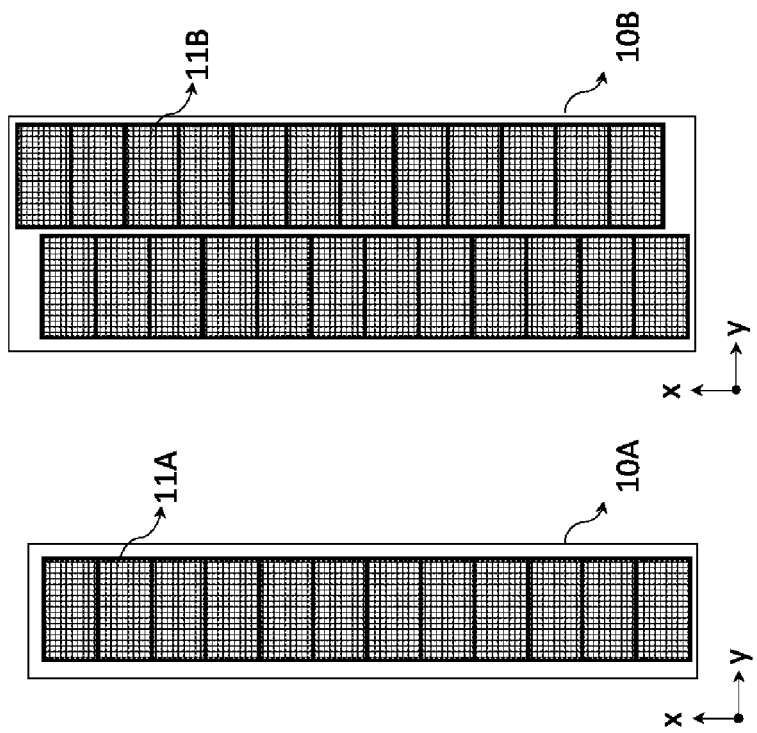
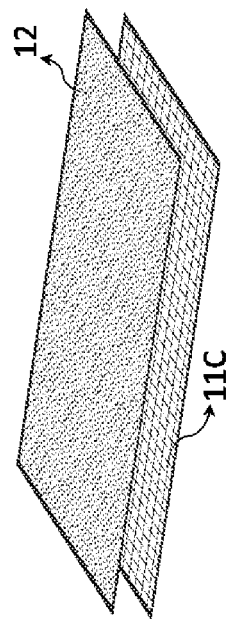

MULTIPLE ANGLE COMPUTATIONAL WAFER INSPECTION

FIELD OF THE INVENTION

This invention relates generally to wafer inspection and more particularly to computational wafer inspection with multiple angle illumination.

BACKGROUND

Wafer inspection refers to inspecting a semiconductor wafer for abnormalities or defects present on the surface of the wafer. These defects could affect the functionality of integrated circuits (ICs) fabricated on the wafer, leading to decreased production yield of ICs. Detecting defects, identifying their root cause, and eliminating them is of foremost importance in semiconductor fabrication.

The sizes of individual components inside ICs have been decreasing with every new generation of semiconductor technology in order to improve performance while reducing cost, a trend widely known as Moore's law. As components in ICs become smaller, tiny defects that were previously overlooked as being too small to affect IC performance begin to manifest themselves as killer defects that could bring down production yield. Consequently, every next generation technology node comes with the challenge of detecting continually shrinking defect sizes.

Simultaneously, the diameter of wafers used by semiconductor fabs has been increasing in order to accommodate an increasing number of ICs on a single wafer for saving cost. When combined with the decreasing nature of defect sizes, the above mentioned increasing wafer diameters presents next generation semiconductor wafer inspection tools the daunting challenge of detecting continually decreasing defects sizes on a continually increasing surface area.

Traditional dark-field wafer inspection tools illuminate a laser spot on the surface of a wafer and use collection optics with a high numerical aperture to detect scattered radiation. While the width of the laser spot is typically in the order of micrometers, the diameter of the wafer can be as large as 450 mm. In order to cover the entire surface of the wafer, the spot is sequentially scanned to illuminate different regions of the wafer until the entire water is covered. Traditional dark-field wafer inspection tools employ a finite number (typically, less than 5) of photodetectors to detect scattered light.

In traditional dark-field wafer inspection tools, it is difficult to inspect a large area of a wafer at a given time. This is because of two reasons: 1) spot size of laser beam is small, 2) the field of view of collection optics is small. While (1) may be addressed by expanding beam size, addressing (2) is challenging because of the need to have a large numerical aperture to capture light scattered at a wide range of angles. Designing collection optics having a large field of view and a large numerical aperture is a formidable task. Collection optics with large numerical aperture also imposes the constraint of reduced working distance between wafer and collection optics, leading to tight optomechanical tolerances.

A trade-off between inspection throughput (measured in wafers per hour) and defect sensitivity exists in traditional wafer inspection tools. The reason for this trade-off is because defect sensitivity is related to the total energy scattered by a defect. Total scattered defect energy can be modeled by multiplying scattered optical power from defect with the amount of time the spot spends on the defect. Scattered power from defect is proportional to the intensity of illumination on defect. Any attempt to increase defect sensitivity by decreasing spot size (so as to increase illumination intensity) or increasing the amount of time the spot spends on defect directly affects throughput. Reducing spot size increases the number of points the spot needs to traverse on the wafer, thereby increasing overall scan time per wafer. Increasing the amount of time a spot spends on a defect by reducing scanning speed also increases the overall scan time for the wafer. Therefore, in traditional wafer inspection tools, increased defect sensitivity comes at the price of decreased inspection throughput.

Traditional dark-field wafer inspection tools suffer from a number of disadvantages, including: a) low throughput due to two-dimensional scanning; b) complex collection optics due to large numerical aperture; c) reduced defect identification capabilities due to limited number of photodetectors; d) trade-off between numerical aperture and working distance; e) limited field of view; f) trade-off between throughput and defect sensitivity; and g) complex scanning mechanism due to two-dimensional scanning requirement.

Accordingly, there is a need for an improved wafer inspection system that improves wafer throughput; simplifies collection optics; increases defect identification capabilities; decouples trade-off between numerical aperture and working distance; improves field of view; relaxes trade-off between throughput and defect sensitivity; and simplifies scanning mechanism for covering entire wafer surface.

SUMMARY

The invention is a system and method for computational wafer inspection with multiple angle illumination.

In some embodiments, the invention is a system for inspecting a surface, comprising: an electromagnetic radiation incident on a predetermined region of said surface, with said region having an aspect ratio larger than unity; a detector array positioned to capture an image of scattered radiation originating from said region; and a processor configured to compute electromagnetic field of said scattered radiation from said image of scattered radiation and generate an image of region by computational propagation of said electromagnetic field through a predetermined distance, whereby features of said region are captured in said image of region.

In some embodiments, the invention is a method for inspecting a surface, comprising: illuminating a region of said surface, with said region having an aspect ratio larger than unity; capturing an image of scattered radiation originating from said region; and computing electromagnetic field of said scattered radiation from said image of scattered radiation and generating an image of region by computational propagation of said electromagnetic field through a predetermined distance, whereby features of said region are captured in said image of region.

BRIEF DESCRIPTION OF THE DRAWINGS

FIG. 4A shows a detector array comprising an array of image sensors arranged in a column, in accordance with the invention.

FIG. 4B, shows a detector array comprising a matrix of image sensors arranged in two columns, in accordance with the invention.

FIG. 4C illustrates an image sensor comprising a microoptic layer, in accordance with the invention.

DETAILED DESCRIPTION OF THE PREFERRED EMBODIMENTS

Figure 1:
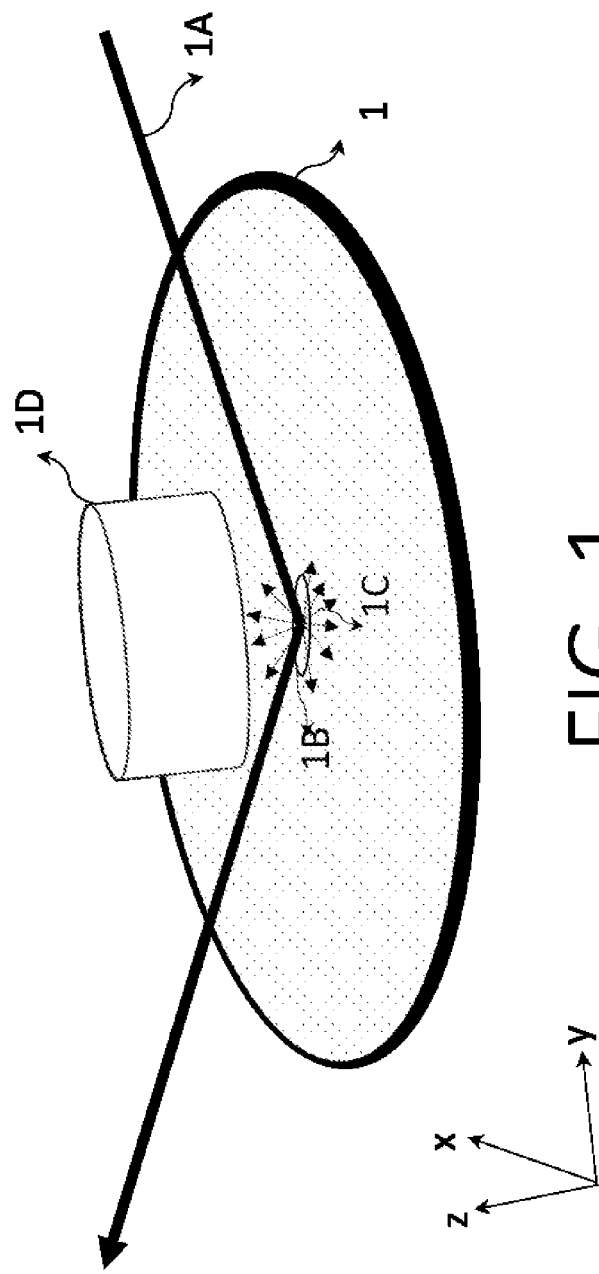
FIG. 1 shows a traditional dark-field wafer inspection system, according to prior art.

FIG. 1 shows a traditional dark-field wafer inspection system, according to prior art. A laser beam 1A illuminates a spot 1B on surface 1. A majority of photons of the laser beam undergo specular reflection when the region of surface 1 under spot 1B is smooth. A feature present on the region under spot 1B generates scattered light 1C. Features include abnormalities or defects and other structures present on surface 1. Surface roughness may also contribute to scattered light 1C. The scattered light 1C may propagate in a wide range of polar and azimuthal angles, depending on the properties of the defect and the roughness of surface. A collection optic 1D with large numerical aperture (higher than 0.9) is used to collect scattered light 1C. The collected light is typically focused on a photodetector, which generates an electrical output that correlates with the total amount of light falling on it. The presence or absence of a defect within the illuminated spot is estimated by applying a threshold on the photodetector output.

The prior art shown in FIG. 1 suffers from a number of drawbacks, including: a) low inspection throughput (number of wafers scanned per hour) due to the requirement to scan a micron sized spot 1B throughout a two dimensional area of surface 1 that can be over a billion times larger than the spot; b) complex collection optics 1D due to the requirement of a large numerical aperture to collect scattered light 1C propagating in a wide range of polar and azimuthal angles; c) reduced defect identification capabilities due to limited number of photodetectors used to detect scattered light 1C collected by collection optic 1D; d) trade-off between numerical aperture of collection optic 1D and working distance, which is the distance between surface 1 and collection optic 1D; e) limited field of view due to small size of spot 1B and small field of view of collection optic 1D, a consequence of its large numerical aperture requirement; f) trade-off between inspection throughput and defect sensitivity due to the dependence of sensitivity on smaller spot size and slower scanning speed; g) complex scanning mechanism due to the two-dimensional scanning requirement of scanning a spot across a two dimensional area with high speed.

Figure 2:
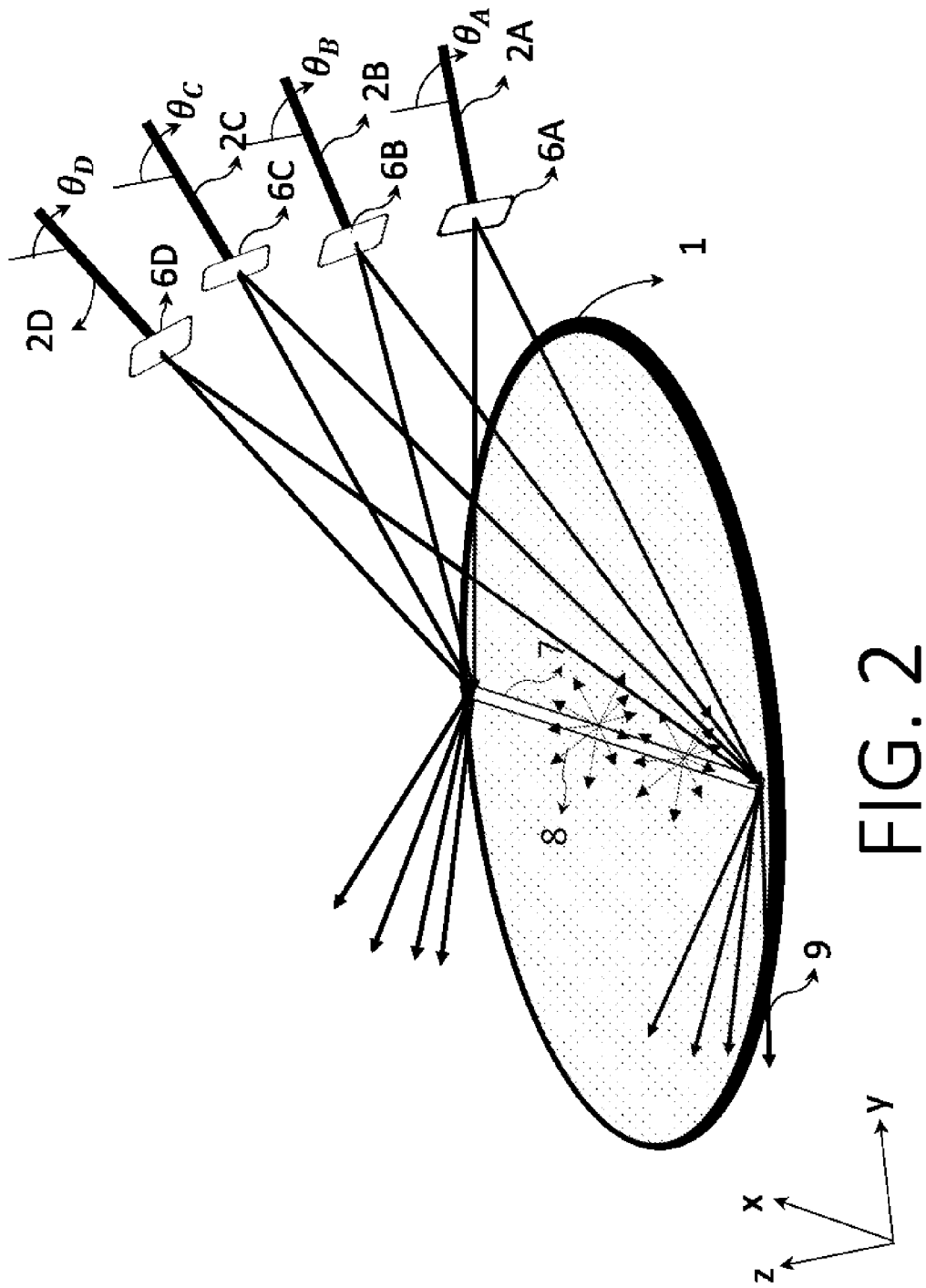
FIG. 2 depicts a multiple angle computational wafer inspection system generating an elongated spot on a predetermined region of surface from multiple angles, in accordance with the invention.

FIG. 2 depicts a multiple angle computational wafer inspection system generating an elongated spot on a predetermined region 7 of surface 1 from multiple illumination angles, in accordance with the invention. An electromagnetic beam 2A, lying on y-z plane, is incident on beam expander 6A to illuminate an elongated spot on region 7 at an angle $\theta_A$ with respect to z axis. Region 7 has an aspect ratio, defined as the ratio of longer dimension (along x axis) to shorter orthogonal dimension (along y axis), larger than unity. In some embodiments, the longer dimension is matched to the diameter of the surface area to be inspected. In addition to beam 2A, three more electromagnetic beams, 2B, 2C, and 2D, are incident on their respective beam expanders, 6B, 6C, and 6D, to illuminate the same region 7. The angles of incidence of all four beams are different. Beam 2B, lying on y-z plane, is incident at an angle of $\theta_B$ with respect to z axis; beam 2C, lying on y-z plane, is incident at an angle of $\theta_C$ with respect to z axis; and beam 2D, lying on y-z plane, is incident at an angle of $\theta_D$ with respect to z axis. The electromagnetic radiation incident on smooth regions of region 7 undergo specular reflection. For example, specular reflection 9 originates from reflection of beam 2A. If there are any defects present on region 7, scattered radiation 8 is generated. Scattered radiation 8 may also have a contribution, called haze, from surface roughness of region 7. Because some amount of surface roughness is typically present throughout surface 1, haze generally manifests as a background signal. Scattered radiation 8 due to a defect, with a size significantly larger than the standard deviation of surface roughness, is typically is stronger than the scattered radiation due to surface roughness.

The intensity profile of scattered radiation from a defect depends on properties of the defect, properties of the incident electromagnetic beam, and the properties of surface 1. Properties of defect includes size of defect, shape of defect, and material of defect. Properties of the incident electromagnetic radiation include angle of incidence, wavelength, polarization, and beam intensity. Properties of surface include roughness and material of surface.

For a given defect on a surface, varying the angle of incidence of the illumination beam has the effect of shifting the intensity profile of scattered radiation. When electromagnetic beams at all four angles, $\theta_A$, $\theta_B$, $\theta_C$, and $\theta_D$, illuminate region 7 at the same time, the scattered radiation 8, originating from a defect present on region 7, comprises of an integration of four shifted intensity profiles. Each of the four intensity profiles of scattered radiation may be obtained by illuminating region 8 with beams, 2A, 2B, 2C, and 2D, individually. The beam expanders, 6A, 6B, 6C, and 6D, may be implemented as a cylindrical lens or a diffractive optical element to expand beams, 2A, 2B, 2C, and 2D, respectively, to have an elongated intensity profile to illuminate region 7.

In some embodiments, the wavelength of electromagnetic beams, 2A, 2B, 2C, and 2D, may be designed to maximize reflected power from surface 1. The reflection coefficient of surface 1 is dependent on the refractive index of surface 1, and the refractive index of surface 1 exhibits a dependence on wavelength. Therefore, the wavelength of the electromagnetic beams can be designed to maximize refractive index, and consequently maximize reflected power, which is the square of reflection coefficient. In some embodiments, the wavelength of the beams are designed to maximize the difference in refractive index between surface 1 and the medium in which the beams propagate immediately before illuminating surface 1. Maximizing this difference in refractive index increases reflected power and scattered intensity from defects. The intensity of scattered light from a defect is inversely proportional to the fourth power of wavelength. Lower wavelengths are therefore more desirable to maximize the intensity scattered radiation. In some embodiments, the wavelength of electromagnetic radiation is chosen as the smallest wavelength that maximizes the refractive index of surface 1. In other embodiments, the wavelength of electromagnetic radiation is chosen as the wavelength at which the intensity of scattered radiation from a defect located on surface 1 is maximized. In some embodiments, the wavelengths of electromagnetic beams, 2A, 2B, 2C, and 2D, are different from each other, so that radiation from respective beams may be separated through filtering prior to detection. In other embodiments, the wavelengths of electromagnetic beams, 2A, 2B, 2C, and 2D, are identical.

In some embodiments, the polarization of electromagnetic beams, 2A, 2B, 2C, and 2D, may be designed to maximize reflected power from surface 1. In some embodiments, a s-polarization (perpendicular to the plane of incidence) is used for the beams to maximize reflected power from surface 1. S-polarized beam also maximizes scattered light 8 originating from a defect in region 7. In some embodiments, the angle of incidence of electromagnetic beams, 2A, 2B, 2C, and 2D, may be designed to maximize reflected power from surface 1. The reflection coefficient of surface 1 increases as the angle of incidence of a beam increases.

Figure 3:
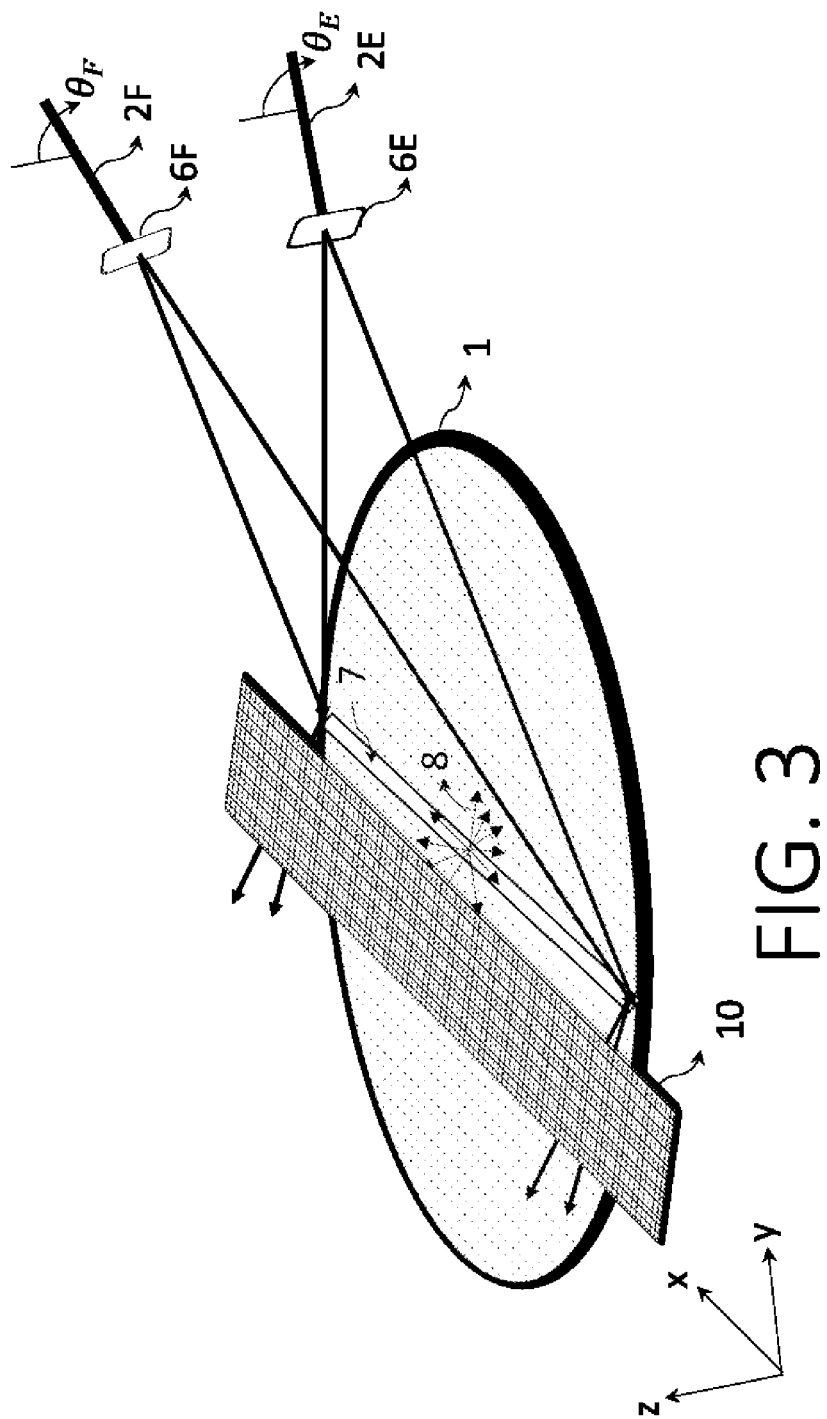
FIG. 3 shows a detector array positioned to capture scattered radiation from an illuminated region on a surface, in accordance with the invention.

FIG. 3 shows a detector array 10 positioned to capture scattered radiation 8 from region 7 on surface 1, in accordance with the invention. The detector array 10 comprises a two dimensional array of photo detectors. The detector array is longer along x axis than it is along the y axis, in order to match the overall shape of region 7. Because of its rectangular shape, the detector array is able to capture a wide range of scattering angles lying on the xz plane, and a relatively narrow range of scattering angles lying on the yz plane. However, the angle of incidence of electromagnetic beams can be used to effectively detect a wide range of scattering angles along yz plane. The scattered intensity profile of a defect is dependent on the angle of incidence of an electromagnetic beam incident on it. As the angle of incidence of the beam is varied, the scattered intensity profile of the defect exhibits a shift. The amount of shift in the scattered intensity profile is related to the amount of variation in the angle of incidence of beam. Consider a scenario in which region 7 on surface 1 is illuminated only by electromagnetic beam 2E, lying on y-z plane, with an angle of incidence of $\theta_E$ with respect to z axis. The detector array 10 captures a wide range of angles along xz plane, but only a narrow range of angles along the yz plane. In other words, because of the small size of detector array 10 along the y dimension, the detector array is unable to detect a wide range of scattering angles along the yz dimension. Nevertheless, this limited yz scattering angle range can be synthetically extended by using multiple electromagnetic beams to illuminate region 7. For example, consider region 7 on surface 1 now illuminated only by electromagnetic beam 2F, lying on y-z plane, with an angle of incidence of $\theta_F$ with respect to z axis. Because of the difference in incidence angles of beams 2E and 2F, the scattered intensity profile due to electromagnetic beam 2F is a shifted version of the scattered intensity profile generated by electromagnetic beam 2E. The direction of shift depends on the differences in polar and azimuthal angles of beams 2E and 2F. Since both beams, 2E and 2F, lie on the y-z plane, their azimuthal angles are the same. The difference in incidence angles of beams, 2E and 2F, is therefore only in the polar angle. Accordingly, the shift of scattered intensity is along y axis. The magnitude of the shift in scattered intensity is proportional to the magnitude of the difference in angle between beams 2E and 2F. A smaller difference in angle results in a smaller shift, and a larger angular difference results in a larger shift. The shift in scattered intensity due to electromagnetic beam 2F allows detector array 10 to detect a range of scattering angles (along yz plane) that was previously not captured from electromagnetic beam 2E. In some embodiments, beams with multiple angles of incidence may be used to allow detector array 10 to capture all scattering angles that would otherwise be missed if only one beam were to be used. The data captured by detector array 10 from multiple angles may then be processed to compute a synthetic data matrix that has a wide extent along both x and y dimensions. The wide extent along x dimension is because of the physical length of detector array 10 along the x dimension, and the wide extent along y dimension is because of the synthetic combination of data from multiple illumination angles. In some embodiments, electromagnetic beams, 2E and 2F, are incident on region 7 simultaneously. When incident simultaneously, the scattered radiation detected by detector array 10 comprises a wide range of angles on y-z plane that are compressed within a small physical extent of detector array 10 along y dimension. In other embodiments, electromagnetic beams, 2E and 2F, are incident on region 7 at different times.

In some embodiments, electromagnetic beams, 2E and 2F, have a wavelength that maximizes quantum efficiency of detector array 10. Quantum efficiency of a photodetector is the ratio of the number of photoelectrons detected by the photodetector to the number of photons incident on the photodetector. Quantum efficiency of a detector exhibits a dependence on wavelength of electromagnetic radiation incident on it. The sensitivity of the photodetector, defined as the smallest detectable number of photons, and the signal to noise ratio of the photodetector can be maximized by choosing a wavelength that maximizes the quantum efficiency of the photodetectors. Maximizing the quantum efficiency of photodetectors present in detector array 10 improves the quality of images detected by detector array 10.

FIG. 4A shows a detector array 10A comprising an array of image sensors 11A arranged in a column, in accordance with the invention. The image sensor 11A may include a complementary metal oxide semiconductor (CMOS) type imager or a charge coupled device (CCD) type imager. Each image sensor 11A comprises a plurality of photodetectors, called as pixels, arranged in a two dimensional array. In some embodiments, image sensor 11A comprises a color filter layer to match the wavelength of electromagnetic beams illuminating the surface. In some embodiments, the color filter layer may comprise multiple wavelength filters that match the wavelengths of incident electromagnetic beams having different angles. The color filters help in separating scattered radiation according to the incidence angles of their illumination beams. For example, a scattered radiation that passes through a given wavelength filter may be associated with an electromagnetic beam having a particular angle of incidence. In some embodiments, image sensor 11A may comprise a polarization filter layer to match the polarization of electromagnetic beams illuminating the surface. In some embodiments, the polarization filter layer may comprise multiple polarization filters that match the polarizations of incident electromagnetic beams having different angles. The polarization filters help in separating scattered radiation according to the incidence angles of their illumination beams. For example, a scattered radiation that passes through a given polarization filter may be associated with an electromagnetic beam having a particular angle of incidence. In some embodiments, all image sensors within detector array 10 have similar imaging settings such as exposure time and gain.

FIG. 4B, shows a detector array 10B comprising a matrix of image sensors 11B arranged in two columns, in accordance with the invention. While the image sensors in each of the two columns are aligned along x axis, the image sensors are designed to be misaligned along the y axis. This allows dead spaces between two image sensors in column 1 to be compensated by an image sensor in column 2, so that no row of detector array 10 is completely blocked. Similarly, dead spaces between two image sensors in column 2 is compensated by an image sensor in column 1. The image sensor 11B may include a complementary metal oxide semiconductor (CMOS) type imager or a charge coupled device (CCD) type imager. Each image sensor 11B comprises a plurality of photodetectors, called as pixels, arranged as a two dimensional array. In some embodiments, image sensor 11B comprises a color filter layer to match the wavelength of electromagnetic beams illuminating the surface. In some embodiments, the color filter layer may comprise multiple wavelength filters that match the wavelengths of incident electromagnetic beams having different angles. The color filters help in separating scattered radiation according to the incidence angles of their illumination beams. For example, a scattered radiation that passes through a given wavelength filter may be associated with an electromagnetic beam having a particular angle of incidence. In some embodiments, image sensor 11B may comprise a polarization filter layer to match the polarization of electromagnetic beams illuminating the surface. In some embodiments, the polarization filter layer may comprise multiple polarization filters that match the polarizations of incident electromagnetic beams having different angles. The polarization filters help in separating scattered radiation according to the incidence angles of their illumination beams. For example, a scattered radiation that passes through a given polarization filter may be associated with an electromagnetic beam having a particular angle of incidence. In some embodiments, all image sensors within detector array 10B have similar imaging settings such as exposure time and gain.

FIG. 4C illustrates an image sensor 11C comprising a microoptic layer 12, in accordance with the invention. The microoptic layer comprises a plurality of lenses implemented as a refractive optical element or a diffractive optical element. In some embodiments, each lens of the microoptic layer generates a focused spot on the pixels of image sensor 11C. A finite number of pixels are allocated for each lens on the microoptic layer 12. The pixels allocated for a lens are centered on the optical axis of the lens. From the position of the focused spot within the pixels allocated for a lens, the phase gradient of scattered radiation incident on the lens can determined. For example, if the focused spot is in the center of the allocated pixels (on the optical axis of lens), then the scattered light can be determined to have zero phase gradient at the surface of the lens. Alternatively, if the focused spot is not at the center, then the scattered light can be determined to have a linear phase gradient that is proportional to the distance between the focused spot and the center of allocated pixels. Accordingly, a phase gradient value can be calculated for each lens of the microoptic layer. By combining phase gradients of all lenses in the microoptic layer using a stitching algorithm, a phase gradient profile for the entire surface of the microoptic layer can be determined. The phase profile of scattered radiation, $P(x,y)$, is then obtained by integrating the phase gradient profile in two dimensions. The intensity of scattered light, $I(x,y)$, is obtained from the intensity of focused spots detected by image sensor 11C. The electromagnetic field of scattered light, $C(x,y)$, is calculated by combining the intensity of scattered radiation, $I(x,y)$, with the phase of scattered radiation, $P(x,y)$, as, $C(x,y) = \sqrt{I(x,y)} e^{(-iP(x,y))}$.

Figure 5:
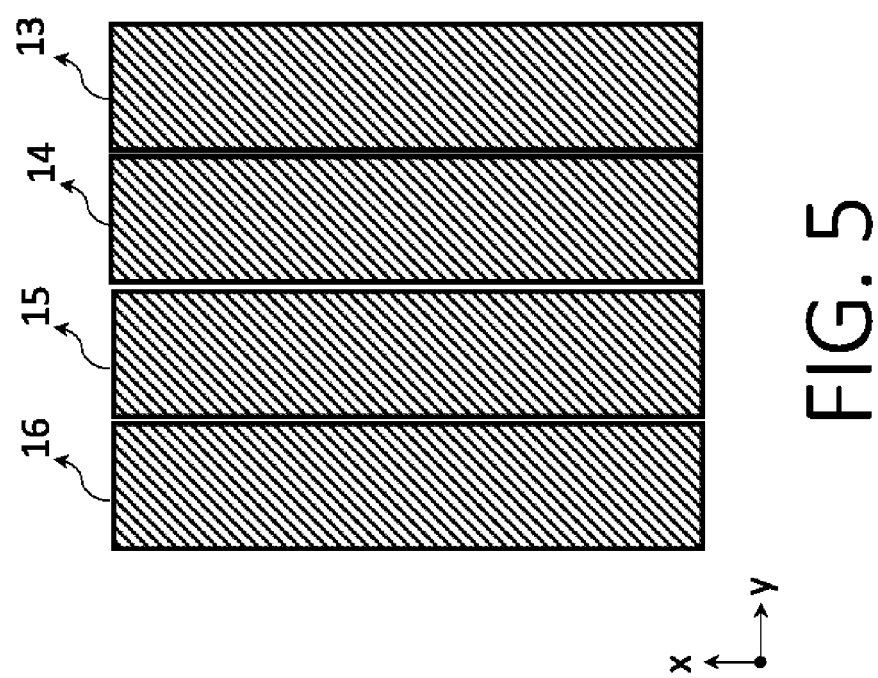
FIG. 5 illustrates stitching of images from detector array in a spatial frequency domain, in accordance with the invention.

FIG. 5 illustrates stitching of images from detector array in a spatial frequency domain, in accordance with the invention. In some embodiments, image data captured by detector array with electromagnetic beams having different illumination angles are stitched along the y dimension. This allows extension scattering angles captured along y axis. Images, 13, 14, 15, and 16, were acquired with different incidence angles. In some embodiments, image data from detector array is converted into an electromagnetic field before stitching. When electromagnetic beams having different angles of incidence are illuminated on a surface at different times, scattered intensity profiles can be readily separated according to the angle of incidence of their respective electromagnetic beams. In this case, the image or electromagnetic field data 13, 14, 15, and 16 would be acquired at different times. Alternatively, when the electromagnetic beams having different angles of incidence are illuminated on a surface at the same time, the image detected by detector array includes scattered intensity profiles originating from all electromagnetic beams. In this case, individual scattering profiles may be separated by coding individual beams having different angles of incidence with different wavelengths, and by using color filters on detector array to separate scattered intensity profiles originating from beams having different incident angles. Alternatively, individual scattering profiles may be separated by coding individual beams having different angles of incidence with different polarizations, and by using polarization filters on detector array to separate scattered intensity profiles originating from beams having different incident angles. The separated scattered intensity profiles corresponding to beams with different incident angles may then be stitched along the y axis. Alternatively, electromagnetic field may be computed from each of the separated scattered intensity profiles, and the electromagnetic fields from scattered intensity profiles corresponding to different angles of incidence may be stitched along the y-axis.

Figure 6:
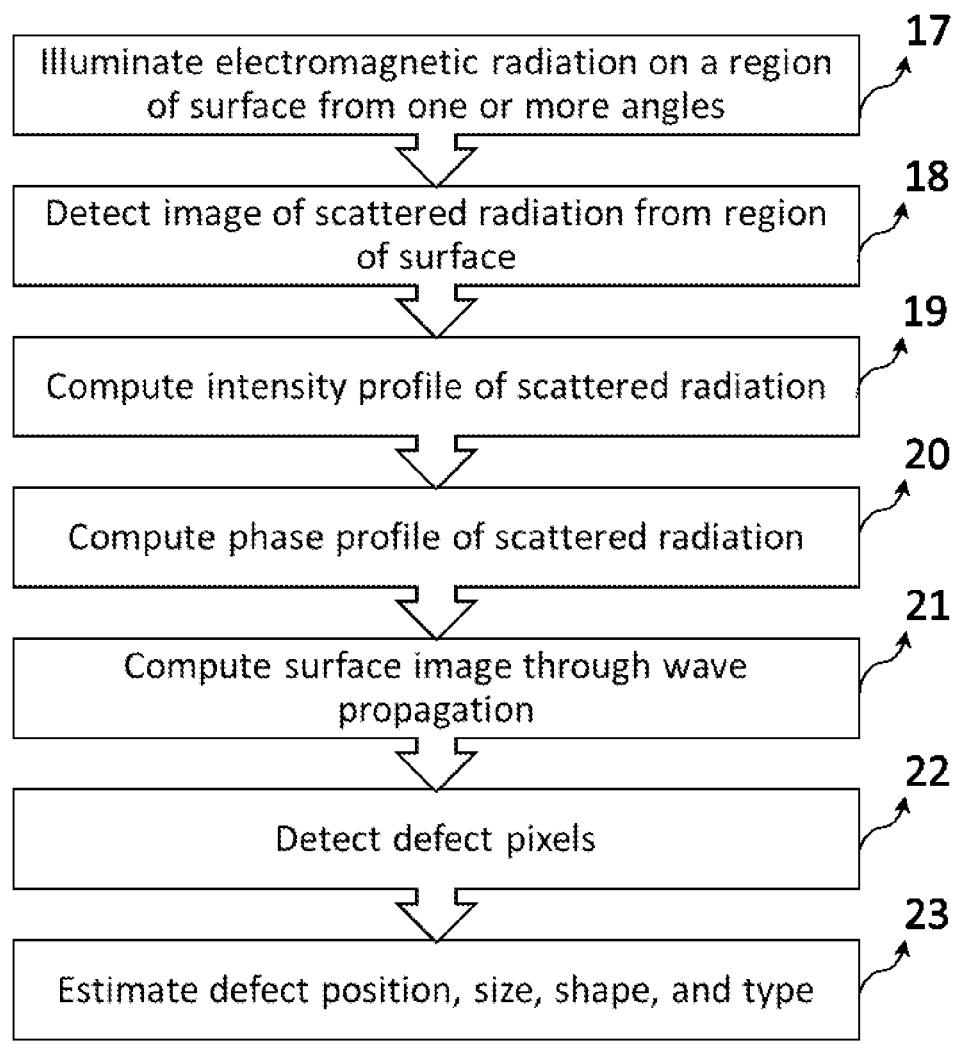
FIG. 6 shows an exemplary flow chart describing steps for computing an image of surface by processing images captured from a detector array for the purpose of estimating defect properties, in accordance with the invention.

FIG. 6 shows an exemplary flow chart describing steps for computing an image of surface by processing images captured from a detector array for the purpose of estimating defect properties, in accordance with the invention. In block 17, a region of surface, with aspect ratio larger than unity, is illuminated with electromagnetic beams or radiation having one of more angles of incidence. In some embodiments, beams having multiple angles of incidence are illuminated at different times. In other embodiments, beams having multiple angles of incidence are illuminated simultaneously. In some embodiments, beams having multiple angles of incidence have similar wavelengths. In other embodiments, beams having multiple angles of incidence have different wavelengths. In some embodiments, beams having multiple angles of incidence have similar polarizations. In other embodiments, beams having multiple angles of incidence have different polarizations. Defects and surface roughness present in the illuminated surface region scatter radiation from incident beams.

In block 18, one or more images of scattered radiation originating from an illuminated region of surface is captured by a detector array. In some embodiments, the detected image comprises information about intensity profile of scattered radiation. In other embodiments, the detected image comprises information about intensity profile and phase profile of scattered radiation. In some embodiments, the detected image comprises information about intensity profile and phase profile of scattered radiation, along with information on the angle of incidence of electromagnetic beam corresponding to scattered radiation.

In block 19, intensity profile of scattered radiation is computed from one or more images captured from a detector array. In some embodiments, the intensity profile of scattered radiation is obtained by separating intensity profiles of scattered radiation originating from electromagnetic beams with multiple angles of incidence. The separated intensity profiles are then stitched to form an extended intensity profile. In other embodiments, the intensity profile of scattered radiation comprises an integration of intensity profiles of scattered radiation originating from electromagnetic beams having multiple angles of incidence.

In block 20, phase profile of scattered radiation is computed from one or more images captured from a detector array. In some embodiments, the phase profile of scattered radiation is obtained by separating phase profiles of scattered radiation originating from electromagnetic beams with multiple angles of incidence. The separated phase profiles are then stitched to form an extended phase profile. In other embodiments, the phase profile of scattered radiation comprises an integration of phase profiles of scattered radiation originating from electromagnetic beams having multiple angles of incidence. Phase profile of scattered radiation may be measured by using a detector array comprising a microoptic layer having an array of lenses. Alternatively, phase profile may also be measured by capturing intensity profiles at two or more different optical path lengths from the illuminated region of surface, and by estimating the phase profile that best satisfies the transport of intensity equation. In some embodiments, optical patch length between detector array and surface may be varied by using a detector array comprising a liquid crystal layer. In other embodiments, optical path length between detector array and surface may be varied by inserting a uniform phase plate, such as a glass plate, between detector array and surface. In some embodiments, the optical path length between the detector array and the surface may be varied by changing the distance between detector array and surface. In some embodiments, an iterative optimization algorithm may be used to estimate phase profile by starting with a random initial estimate for phase and arriving at a final estimate by propagating the electromagnetic field at detector array, initially obtained by combining intensity profile and random phase profile, between two image planes separated by the optical path length.

In block 21, one or more images of a surface region is computed by first combining the intensity and phase profiles to form an electromagnetic field, and then by propagating the complex electromagnetic field through a predetermined distance. In some embodiments, the image of surface region is a focused image obtained by propagating the complex electromagnetic field through a distance equal to the optical path length between the surface and the detector array. In other embodiments, the image of surface region is a defocused image obtained by propagating the complex electromagnetic field through a distance close, but not equal to, the optical path length between the surface and the detector array. The electromagnetic field at the detector array is computationally propagated to the surface. In some embodiments, computational propagation is performed in the spatial frequency domain using steps comprising: computing spatial frequencies of electromagnetic field using a transformation; computing a propagation transfer function; and computing the product of spatial frequencies with propagation transfer function. In some embodiments, computing spatial frequencies of an electromagnetic field comprises computation of $\tilde{C}(k_x, k_y) = F\{C(x, y)\}$, where $C(x,y)$ is the electromagnetic field, $F$ refers to Fourier transform, and $\tilde{C}(k_x, k_y)$ refers to the spatial frequency of $C(x,y)$. Propagation transfer function, $\tilde{H}(k_x, k_y)$, is calculated as $$\tilde{H}(k_x, k_y) = e^{\left(i\Delta z \sqrt{(k^2 - k_x^2 - k_y^2)}\right)},$$

where $k = 2\pi n/\lambda$, n is refractive index, $\lambda$ is the wavelength of the electromagnetic beam, and $\Delta z$ is the distance through which the electromagnetic field needs to be propagated. Computing the product of said spatial frequencies with said propagation transfer function refers to multiplying $\tilde{C}(k_x, k_y)$ with $\tilde{H}(k_x, k_y)$. Finally, the electromagnetic field after propagation is computed as, $F^{-1}\{\tilde{C}(k_x, k_y)\tilde{H}(k_x, k_y)\}$, where $F^{-1}$ refers to inverse Fourier transform. In other embodiments, computational propagation of an electromagnetic field is performed by first computing an impulse response of propagation and then computing a convolution of the electromagnetic field with the impulse response. The impulse response of propagation is computed as $$F^{-1}\{e^{\left(i\Delta z \sqrt{(k^2 - k_x^2 - k_y^2)}\right)}\}.$$

In some embodiments, a plurality of images of surface regions obtained at different surface locations may be combined to form an image of surface. In some embodiments, a surface may be rotated relative to an electromagnetic beam so that the electromagnetic beam is incident on a plurality of regions of surface when the surface is rotated. Rotation of a surface may be achieved by holding the surface in place with a chuck, and rotating or spinning the chuck. In other embodiments, a surface may be translated relative to an electromagnetic beam so that the electromagnetic beam is incident on a plurality of regions of the surface when the surface is translated. Translation of a surface may be achieved by holding the surface in place with a chuck, and translating the chuck.

In block 22, one or more images of surface is used to detect defect pixels from their background pixels. In some embodiments, a focused image of surface is used for detecting defect pixels because of high intensity values of defect pixels in focused images. In a focused image of a surface, defect pixels may be separated from their background pixels by thresholding all image pixel values with a threshold value. To minimize false positives, the threshold value should be higher than background pixel values in the pixel region surrounding defect pixels. The value of a threshold may be adaptively chosen depending on local background values. Accordingly, the threshold value in a high background region is higher than the threshold value in a lower background region. In some embodiments, the shape of a focused defect may be modeled and the model shape may be correlated with image of surface to create correlation peaks at the position of defects. Correlation peaks may be separated from their background using thresholding. For each defect, a defect pixel region containing a predetermined number of pixels surrounding the detected defect pixels is segmented for identification of the defect by estimating its properties.

In block 23, each defect pixel region is further processed to identify the defect by estimating defect properties such as position on wafer, size, shape, and type. One or more images of surface, including focused and defocused images, may be used for estimating defect properties. The position of a defect on a surface may be accurately estimated by fitting a model of defect on the defect pixel region. Error values between model and defect pixels may be computed for a variety of positions. The position with least error value is determined as the position of defect on surface. In some embodiments, the position of a defect may also be determined using a position parameter such as peak, centroid, or midpoint of the defect pixel region. The size of defect may be calculated by measuring the width of the defect along one, two, or three dimensions from multiple focused and defocused images of surface. Size of defect may refer to length, area, or volume of a defect. The shape of a defect may be obtained from defect pixel regions in multiple focused and defocused images. In some embodiments, a defocused image of a surface may comprise more information about the shape of defect than a focused image. This is because scattered radiation from defect falls on more number of pixels in a defocused image than in a focused image. The defect pixels may be compared with models of focused and defocused defect pixel profiles. Comparisons may include both pixel intensity and pixel phase. Models may include scaled, rotated, translated, and other deformed versions of numerous known defect types such as particles, process induced defects, ellipsoids, crystal originated pits (COP), bumps, scratches, and residues. An error metric may be computed by calculating the difference between defect pixels and models. The model with the least error may be declared as an estimate of defect type.

Figure 7:
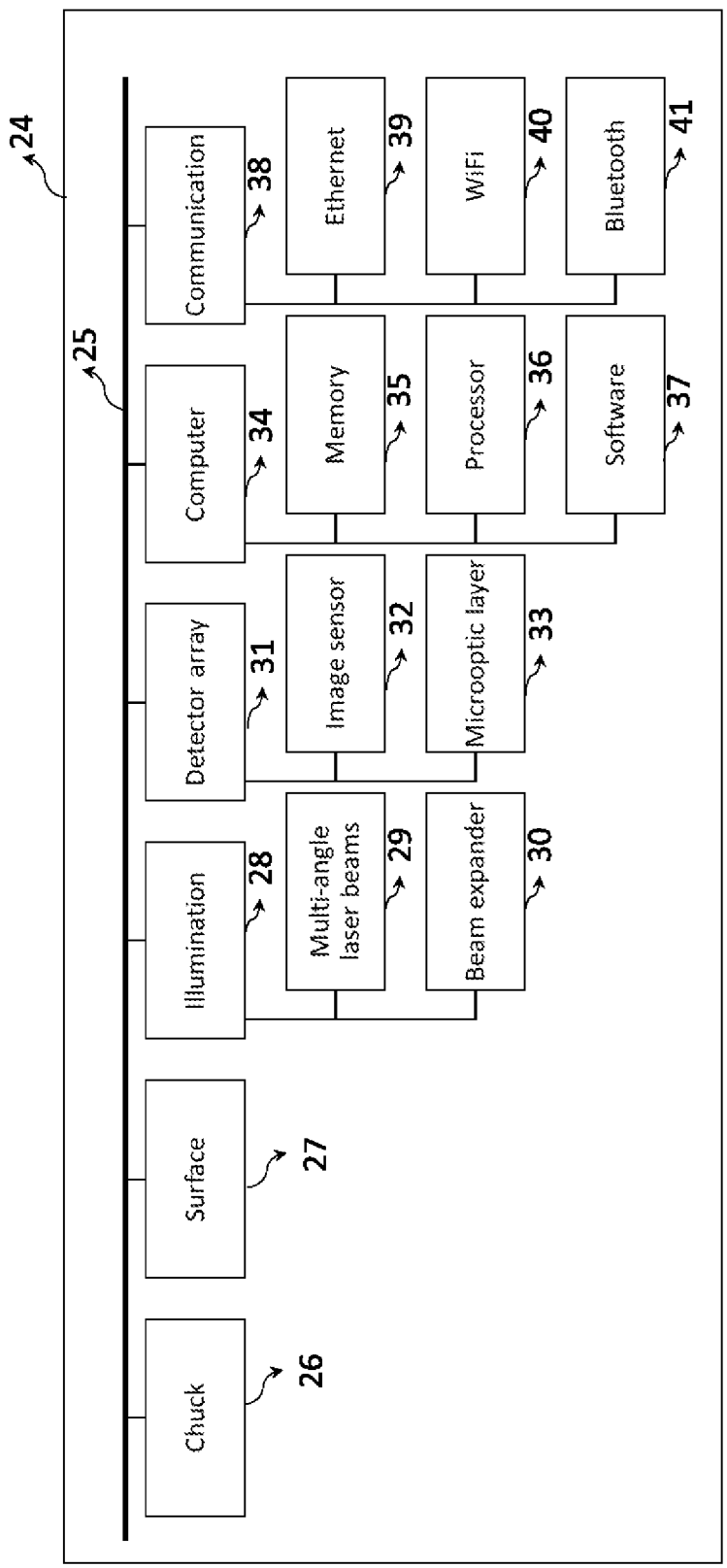
FIG. 7 illustrates a block diagram of a system for multiple angle computational wafer inspection, in accordance with the invention.

FIG. 7 illustrates a block diagram of a system 24 for multiple angle computational wafer inspection, in accordance with the invention. A bus 25 connects various blocks of system 24, namely chuck 26, surface 27, illumination 28, detector array 31, computer 34, and communication 38. Data and control signals are carried by bus 24. Chuck 25 includes an edge handling system that holds the edge of surface, vacuum system that holds the back side of surface with vacuum suction, gas vents, and support structures used to hold surface 27 flat. Surface 27 comprises the region to be illuminated by system 24. Surface 27 may be flat, curved due to gravity induced sag, or deformed due to coatings. Illumination 28 includes multiple laser beams 29 and beam expanders 30. Detector array 31 comprises multiple image sensors 32, microoptic layer 33, color filter layer, and a polarization filter layer. Detector array 31 captures scattered radiation from surface and transfers image data through bus 25 to computer 34. Detector array 31 receives control information to adjust parameters such as exposure time and gain from computer through bus 25. Computer 34 includes a processor 36, memory 35, and software 37. Software 37 processes image data from detector array to compute a number of entities, including: intensity and phase profiles of electromagnetic field; wave propagation to compute surface region image; surface image by combining a plurality of surface region images; defect pixel region; defect properties such as position, size, shape, and type. Software 37 generates control information and sends them through bus 25 to chuck 26, surface 27, detector array 31, and illumination 28. Computer 34 connects to communication block 38 for communicating data and control information through bus 25. Communication block 38 includes Ethernet 39, WiFi 40, and Bluetooth 41.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. An inspection system for capturing a feature on a surface, comprising:
   an electromagnetic radiation incident on a predetermined region of said surface comprising said feature, with said region having an aspect ratio larger than unity;
   a scattered radiation originating from said region;
   a detector array having an aspect ratio larger than unity positioned to capture said scattered radiation to form an image of scattered radiation;
   a computer configured to
      estimate phase of scattered radiation and intensity of scattered radiation at said detector array from said image of scattered radiation;
      combine said intensity of scattered radiation with said phase of scattered radiation to compute electromagnetic field at said detector array; and
      propagate said electromagnetic field computationally through a predetermined distance to compute an image of region with aspect ratio larger than unity by determining either propagation transfer function or impulse response of propagation for a medium between said surface and said detector array,
   whereby said feature is captured in said image of region.

2. The system of claim 1, further comprising two or more electromagnetic radiations incident on said region with two or more angles of incidence.

3. The system of claim 1, wherein said computer is configured to combine a plurality of units of said images of region to form an image of surface.

4. The system of claim 1, further comprising means for rotating said surface relative to said electromagnetic radiation so that said electromagnetic radiation is incident on a plurality of regions of said surface when said surface is rotated.

5. The system of claim 1, further comprising means for translating said surface relative to said electromagnetic radiation so that said electromagnetic radiation is incident on a plurality of regions of said surface when said surface is translated.

6. The system of claim 1, wherein said detector array comprises a microoptic layer to detect phase of said scattered radiation.

7. The system of claim 1, wherein said detector array comprises a color filter layer to detect wavelength of scattered radiation.

8. The system of claim 1, wherein said detector array comprises a polarization filter layer to detect polarization of scattered radiation.

9. The system of claim 1, further comprising means for varying optical path length between said detector array and said region so that said scattered radiation is detected at multiple values of optical path length.

10. The system of claim 1, wherein said electromagnetic radiation has a wavelength that maximizes reflected power from said surface.

11. The system of claim 1, wherein said electromagnetic radiation has a polarization that maximizes reflected power from said surface.

12. The system of claim 1, wherein said detector array comprises an array of image sensors.

13. The system of claim 1, wherein said electromagnetic radiation has a wavelength that maximizes quantum efficiency of said detector array.

14. A method for capturing a feature on a surface with an inspection system, comprising:
    illuminating a region of said surface comprising said feature using an electromagnetic radiation, with said region having an aspect ratio larger than unity;
    scattering said electromagnetic radiation to form a scattered radiation originating from said region;
    capturing said scattered radiation to form an image of scattered radiation, having an aspect ratio larger than unity;
    estimating phase of scattered radiation and intensity of scattered radiation from said image of scattered radiation;
    combining said intensity of scattered radiation with said phase of scattered radiation to compute electromagnetic field at the plane of said image of scattered radiation; and
    propagating said electromagnetic field computationally through a predetermined distance to compute an image of region with aspect ratio larger than unity by determining either propagation transfer function or impulse response of propagation for a medium between said surface and said plane of said image of scattered radiation,
    whereby said feature is captured in said image of region.

15. The method of claim 14, wherein said phase of scattered radiation is computed using transport of intensity equation.

16. The method of claim 14, wherein said combining said intensity of scattered radiation with said phase of scattered radiation involves stitching multiple units of said images of scattered radiation.

17. The method of claim 14, wherein said propagating said electromagnetic field computationally comprises: computing spatial frequencies of said electromagnetic field; computing a propagation transfer function; and computing the product of said spatial frequencies with said propagation transfer function.

18. The method of claim 14, wherein said propagating said electromagnetic field computationally comprises computing an impulse response of propagation and computing a convolution of said electromagnetic field with said impulse response of propagation.

19. The method of claim 14, wherein said image of region is a focused or defocused image computed by propagating said electromagnetic field to said surface.

20. The method of claim 14, further comprising detection of feature pixels from said image of region and estimation of feature properties from said feature pixels.

* * * * *